United States Patent [19]

Parg et al.

[11] Patent Number: 4,650,905
[45] Date of Patent: Mar. 17, 1987

[54] DIPHENYL ETHERS AND THEIR USE FOR CONTROLLING UNDESIRABLE PLANT GROWTH

[75] Inventors: Adolf Parg, Bad Durkheim; Gerhard Hamprecht, Weinheim; Bruno Wuerzer, Otterstadt, all of Fed. Rep. of Germany

[73] Assignee: BASF Aktiengesellschaft, Fed. Rep. of Germany

[21] Appl. No.: 774,866

[22] Filed: Sep. 11, 1985

Related U.S. Application Data

[63] Continuation of Ser. No. 568,267, Jan. 4, 1984.

[30] Foreign Application Priority Data

Jan. 11, 1983 [DE] Fed. Rep. of Germany ....... 3300585

[51] Int. Cl.$^4$ ..................... C07C 149/42; A01N 31/00
[52] U.S. Cl. .................................... 564/430; 564/340; 71/121; 71/98
[58] Field of Search .................. 564/430, 340; 71/121, 71/98

[56] References Cited

U.S. PATENT DOCUMENTS

| | | | |
|---|---|---|---|
| 4,039,588 | 8/1977 | Wilson et al. | 564/430 |
| 4,093,446 | 6/1978 | Bayer et al. | 71/109 |
| 4,277,624 | 7/1981 | Yoshimoto et al. | 564/430 |
| 4,358,308 | 11/1982 | Swithenbank | 71/98 |
| 4,364,875 | 12/1982 | Sehring et al. | 260/465 |
| 4,419,124 | 12/1983 | Swithenbank | 71/121 |

FOREIGN PATENT DOCUMENTS 1390295  4/1975  United Kingdom ................ 564/430

*Primary Examiner*—Charles F. Warren
*Assistant Examiner*—John A. Sopp
*Attorney, Agent, or Firm*—Keil & Weinkauf

[57] ABSTRACT

Diphenyl ethers of the formula

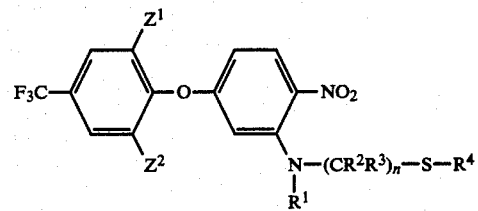

where $Z^1$ is hydrogen or halogen, $Z^2$ is halogen, $R^1$, $R^2$ and $R^3$ are each hydrogen or alkyl, $R^4$ is alkyl or an araliphatic radical and n is a number from 1 to 8, are used for controlling undesirable plant growth.

11 Claims, No Drawings

DIPHENYL ETHERS AND THEIR USE FOR CONTROLLING UNDESIRABLE PLANT GROWTH

This application is a continuation of application Ser. No. 568,267, filed on Jan. 4, 1984.

The present invention relates to diphenyl ethers, herbicides which contain these compounds as active ingredients and their use for controlling undesirable plant growth.

The literature discloses herbicidally active ingredients from the diphenyl ether class which carry an amino radical ortho to the nitro group (German Laid-Open Application DOS No. 2,304,006 and U.S. Pat. No. 4,093,446).

We have found that diphenyl ethers of the formula

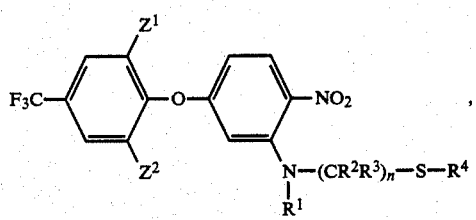

where $Z^1$ is hydrogen or halogen, $Z^2$ is halogen, $R^1$, $R^2$ and $R^3$ independently of one another are each hydrogen or $C_1$–$C_4$-alkyl, $R^4$ is $C_1$–$C_{10}$-alkyl or an araliphatic radical of 7 to 10 carbon atoms, and n is a number from 1 to 8, have a total or selective herbicidal activity, depending on the preparation and dosage.

In formula I, $Z^1$ is hydrogen or halogen, eg. fluorine, chlorine or bromine, $Z^2$ is halogen, eg. fluorine, chlorine or bromine, $R^1$, $R^2$ and $R^3$ independently of one another are each hydrogen or $C_1$–$C_4$-alkyl, eg. methyl, ethyl, n-propyl, i-propyl, n-butyl, i-butyl or tert.-butyl, $R^4$ is $C_1$–$C_{10}$-alkyl, eg. methyl, ethyl, n-propyl, i-propyl, n-butyl, i-butyl, tert.-butyl, n-pentyl, one of the isomeric pentyl radicals, n-hexyl, n-heptyl, n-octyl, n-nonyl, n-decyl or one of the corresponding isomeric alkyl radicals, or an araliphatic radical of 7 to 10 carbon atoms, eg. benzyl or phenethyl, and n is a number from 1 to 8.

If n is >1, the radicals —$CR^2R^3$— in formula I can be different.

Preferred diphenyl ethers are compounds of the formula I where $Z^1$ is hydrogen, $Z^2$ is chlorine, $R^1$ is hydrogen, $R^2$ and $R^3$ independently of one another are each hydrogen or $C_1$–$C_4$-alkyl, $R^4$ is $C_1$–$C_{10}$-alkyl, preferably $C_1$–$C_4$-alkyl, and n is a number from 1 to 4, in particular from 1 to 3.

The compounds of the formula I can be prepared, for example, by the processes below.

The diphenyl ether of the formula I are obtained by reacting a diphenyl ether of the formula

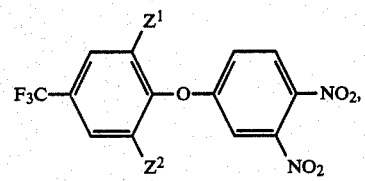

where $Z^1$ and $Z^2$ have the above meanings, with not less than the stoichiometric amount of an amine of the formula

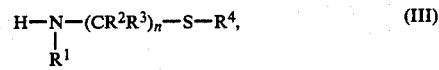

where $R^1$, $R^2$, $R^3$, $R^4$ and n have the above meanings (process a). The reaction is carried out in the presence of an inert organic solvent at from −20° at to +120° C., in particular from 0° to 100° C., under atmospheric or superatmospheric pressure, either continuously or batchwise. The reaction time varies depending on the solvent used and the reaction temperature, and is from 0.5 to 24 hours.

The diphenyl ethers of the formula I are also obtained by reacting a diphenyl ether of the formula

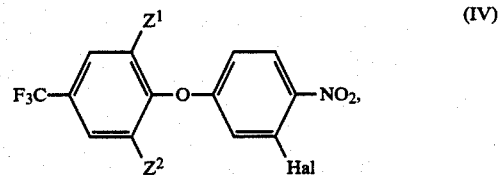

where $Z^1$ and $Z^2$ have the above meanings and Hal is halogen, with not less than the stoichiometric amount of an amine of the formula

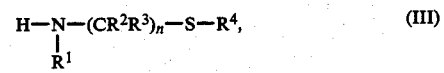

where $R^1$, $R^2$, $R^3$, $R^4$ and n have the above meanings, in an inert organic solvent and in the presence or absence of an acid acceptor (process b). The reaction is carried out at from 20° to 180° C., in particular from 60° to 150° C., under atmospheric or superatmospheric pressure, either continuously or batchwise. The reaction time varies depending on the solvent used and the reaction temperature and is from 2 to 48 hours.

The preparation of the diphenyl ethers of the formula I by process (a) can be represented by the following equation:

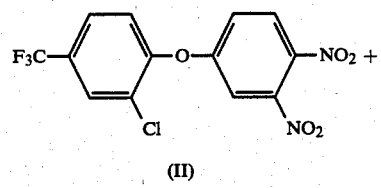

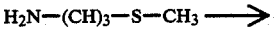

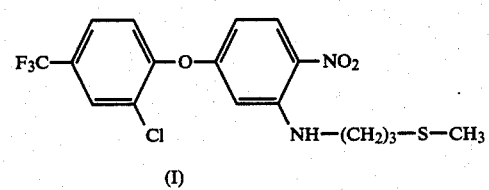

The starting materials are employed in about stoichiometric amounts, but an excess of as much as 200%, based on II, of starting material III is preferred. Advantageously, the process is carried out by adding the starting material III, if appropriate dissolved in an inert organic solvent, to a solution of the dinitrodiphenyl ether II in an inert organic solvent at from −20° to +120° C., preferably from 0° to 100° C.

To complete the reaction, stirring is continued for from 0.5 to 24, preferably from 2 to 12, hours at from 0° to 100° C., after which the reaction mixture is evaporated down and the desired end products can be isolated by reprecipitation or recrystallization or by stirring with water; if necessary, they can be purified by chromatography.

The preparation of the diphenyl ethers of the formula I by process (b) can be represented by the following equation:

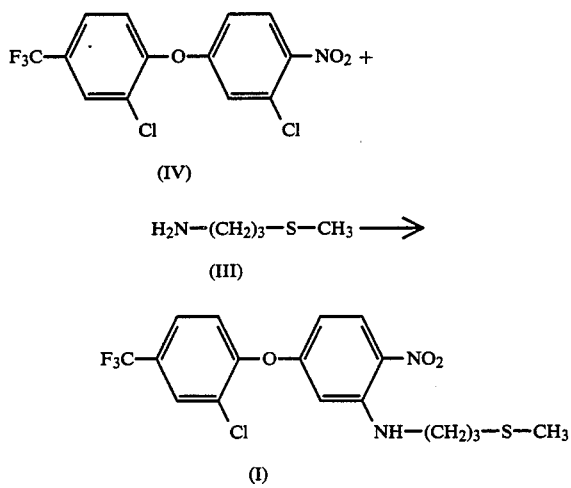

The starting materials are employed in about stoichiometric amounts, ie. from 0.9 to 1.1 moles of starting material III per mole of IV. If necessary, an acid acceptor can be added to complete the reaction, but this function can also be assumed by the starting material III itself. Furthermore, the hydrogen halide formed during the reaction can also be expelled by passing in an inert gas, eg. nitrogen. Advantageously, the process is carried out by mixing a solution of the starting material IV in an inert organic solvent with an equimolar amount of starting material III and the acid acceptor at 20° C., and heating the mixture to 180° C., preferably 60°–150° C., for complete conversion. To complete the reaction, stirring is continued for from 2 to 48, preferably from 8 to 24, hours, after which the reaction mixture is evaporated down or poured onto water, and the desired end products are isolated by extraction or filtration under suction. They can be purified by reprecipitation, recrystallization or chromatrography.

Organic solvents which are inert under the particular reaction conditions are used for both processes. Examples of suitable solvents are halohydrocarbons, in particular chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether, nitrohydrocarbons, eg. nitromethane, nitroethane, nitrobenzene, o-, m- and p-chloronitrobenzene and o-nitrotoluene, nitriles, eg. acetonitrile, butyronitrile, isobutyronitrile, benzonitrile and m-chlorobenzonitrile, aliphatic and cycloaliphatic hydrocarbons, eg. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-triethylpentane, 2,2,3-trimethylpentane, 2,2,3-trimethylpentane and octane, esters, eg. ethyl acetate, ethyl acetoacetate and isobutyl acetate, amides, eg. formamide, methylformamide and dimethylformamide, ketones, eg. acetone and methyl ethyl ketone, and other appropriate mixtures. Advantageously, the solvent is used in an amount of from 100 to 2,000, preferably from 200 to 700, % by weight, based on the starting materials.

Suitable acid acceptors are any conventional ones. These preferably include tertiary amines, alkaline earth metal comounds, ammonium compounds and alkali metal compounds, as well as mixtures of these. However, it is also possible to use zinc compounds. Examples of suitable basic compounds are potassium hydroxide, sodium hydroxide, potassium carbonate, sodium carbonate, lithium hydroxide, lithium carbonate, sodium carbonate, potassium bicarbonate, calcium hydroxide, calcium oxide, barium oxide, magnesium hydroxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium acetate, trimethylamine, triethylamine, tripropylamine, triisopropylamine, tributylamine, triisobutylamine, trisec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, $\alpha$-picoline, $\beta$-picoline, $\gamma$-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, trifurylamine and triethylenediamine.

The starting compounds are prepared by a conventional method. For example, 3,4-dinitrodiphenyl ethers of the formula II are obtained by the procedure described in European Laid-Open Application No. 7,417, while 3-chloro-4-nitrodiphenyl ethers of the formula IV are obtained by the procedure described in German Laid-Open Application DOS No. 2,311,638. The compounds of the formula III are available generally, or can likewise be prepared by a conventional process.

The Examples which follow illustrate the preparation of the compounds of the formula I by the stated processes. Parts by weight bear the same relation to parts by volume as that of the kilogram to the liter.

EXAMPLE 1

15 parts by weight of 3-methylthio-n-propylamine were added to a solution of 18.1 parts by weight of 3,4-dinitro-2'-chloro-4'-trifluoromethyldiphenyl ether in 50 parts by volume of tetrahydrofuran, and the reaction mixture was stirred for a further 3 hours at 60° C. and then evaporated to dryness under reduced pressure. The residue was taken up in diethyl ether, the solution was extracted with dilute hydrochloric acid and water, and the organic phase was dried with magnesium sulfate, filtered and evaporated down under reduced pressure. 19 parts by weight (90% of theory) of 3-[(3''-methylthio-n-propyl)-amino]-4-nitro-2'-chloro-4'-trifluoromethyldiphenyl ether of refractive index $n_D^{25} = 1.6079$ (compound No. 1) were obtained.

EXAMPLE 2

A mixture of 21.1 parts by weight of 3-chloro-4-nitro-2'-trifluoromethyldiphenyl ether, 200 parts by volume of pyridine, 15.3 parts by weight of sodium bicarbonate and 11.3 parts by weight of (1-methyl-2-methylthioethyl)-amine were stirred for 24 hours at 100° C. After the reaction solution had cooled, it was stirred into water, the oil which separated out was taken up in methylene chloride, and the solution was extracted with dilute hydrochloric acid and water. The organic phase was dried with magnesium sulfate, filtered, and evaporated to dryness under reduced pressure. 22 parts by weight (87% of theory) of 3-[(1'''-methyl-2'''-methylthioethyl)-amino]-4-nitro-2'-chloro-4'-trifluoromethyldiphenyl ether of refractive index $n_D^{25} = 1.6013$ (compound No. 2) were obtained.

For example, the compounds below can be obtained by a similar method:

ous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredients, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol

| Compound no. | $Z^1$, $Z^2$ | $-N(R^1)-(CR^2R^3)_n-S-R^4$ | M.p.[°C.]; $n_D^{25}$ wavelength of a band in the infrared spectrum |
|---|---|---|---|
| 3 | 2-chloro-4-trifluoromethylphenyl | (2-methylthio-ethyl)-amino | 94–96 |
| 4 | 2-chloro-4-trifluoromethylphenyl | (2-ethylthio-ethyl)-amino | 1.5821 |
| 5 | 2-chloro-4-trifluoromethylphenyl | (1-methyl-2-ethylthio-ethyl)-amino | 1.5898 |
| 6 | 2-chloro-4-trifluoromethylphenyl | (1-methyl-2-propylthio-ethyl)-amino | 1.5848 |
| 7 | 2-chloro-4-trifluoromethylphenyl | (1,1-dimethyl-2-methylthio-ethyl)-amino | 1.5842 |
| 8 | 2-chloro-4-trifluoromethylphenyl | (2-n-octylthio-ethyl)-amino | 1.6092 |
| 9 | 2-chloro-4-trifluoromethylphenyl | (1-ethyl-2-methylthio-ethyl)-amino | 1.5973 |
| 10 | 2-chloro-4-trifluoromethylphenyl | (2-benzylthio-ethyl)-amino | 1.6181 |
| 11 | 2-chloro-4-trifluoromethylphenyl | (2-ethylthio-n-propyl)-amino | 1.5829 |
| 12 | 2-chloro-4-trifluoromethylphenyl | (1-ethyl-2-ethylthio-ethyl)-amino | |
| 13 | 2-chloro-4-trifluoromethylphenyl | (2-methylthio-n-butyl)-amino | |
| 14 | 2-chloro-4-trifluoromethylphenyl | (2-ethylthio-n-butyl)-amino | |
| 15 | 2-chloro-4-trifluoromethylphenyl | (2-n-propylthio-propyl)-amino | |
| 16 | 2-chloro-4-trifluoromethylphenyl | (2-n-butylthio-n-propyl)-amino | |
| 17 | 2-chloro-4-trifluoromethylphenyl | (2-methylthio-n-butyl)-amino | |
| 18 | 2-chloro-4-trifluoromethylphenyl | (2-ethylthio-n-butyl)-amino | |
| 19 | 2-chloro-4-trifluoromethylphenyl | (2-phenethylthio-n-propyl)-amino | |
| 20 | 2-chloro-4-trifluoromethylphenyl | (1,1-dimethyl-2-methylthio-n-propyl)-amino | |
| 21 | 2-bromo-4-trifluoromethylphenyl | (2-methylthio-n-propyl)-amino | |
| 22 | 2,6-dichloro-4-trifluoromethylphenyl | (2-methylthio-n-propyl)-amino | |

The diphenyl ethers of the formula I may be applied for instance in the form of directly sprayable solutions, powders, suspensions (including high-percentage aqueethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulose powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 10 parts by weight of compound no. 2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 10 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 4 dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 6 is well mixed with 3 parts by weight of the sodium salt of diisobutylnapthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 3 is intimately mixed with 95 parts by weight of particulate kaolin. A dust is obtained containing 5% by weight of the active ingredient.

VII. 30 parts by weight of compound no. 11 is intimately mixed with a mixture consisting of 92 parts of weight of powdered silica gel and 8 parts by weight of paraffin oil which has been sprayed onto the surface of this silica gel. A formulation of the active ingredient is obtained having good adherence.

VIII. 20 parts of compound no. 9 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well when they are applied postemergence, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, the type of soil and the application method employed, and varies from 0.005 to 3 kg/ha and more, but is preferably from 0.01 to 1.0 kg/ha.

The herbicidal action of diphenyl ethers of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. The application rate was either 0.03 or 0.06 kg of active ingredient per hectare.

The pots were set up in the greenhouse-species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Amaranthus spp., *Chenopodium album, Euphorbia geniculata, Galium aparine, Hordeum vulgare, Lamium amplexicaule, Oryza sativa, Sesbania exaltata, Sinapis alba, Solanum nigrum, Triticum aestivum,* and *Viola tricolor.*

The prior art herbicidal active ingredients 3-methylamino-4-nitro-2'-chloro-4'-trifluoromethyl-diphenyl ether (A; German Laid:Open Application No. DE-OS 2,304,006) and 3-[(2-hydroxyethyl)-amino]-4-nitro-2'-chloro-4'-trifluoromethyl-diphenyl ester (B; U.S. Pat. No. 4,093,446) were used for comparison purposes.

Investigations into herbicidal properties or preemergence application revealed that for example compounds nos. 2, 9 and 10 had a good action at an application rate of 3.0 kg/ha.

On postemergence application, for instance compounds nos. 1, 2, 3, 5, 6, 7 and 9 combatted broadleaved weeds very well at a rate of 0.06 kg/ha. Compounds nos. 1 and 9 were tolerated by rice much better than the prior art compounds A and B, and also had a better action on broadleaved plants, e.g., Sesbania exaltata. Further, for example compounds nos. 1, 9 and 11, at a rate of only 0.03 kg/ha, combatted unwanted broadleaved plants and were selective in crops such as cereals and rice. Leaf scorch on the crop plants was tolerable and did not result in any permanent damage.

In view of the numerous application methods possible, the diphenyl ethers of the formula I may be used in a large number of crops for removing unwanted plant growth, especially broadleaved annual species. The following crops may be mentioned by way of example:

| Botanical name | Common name |
| --- | --- |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | |
| Brassica napus var. rapa | turnips |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum | tobacco |
| (N. rustica) | |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the diphenyl ethers of the formula I, or agents containing them, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A diphenyl ether of the formula

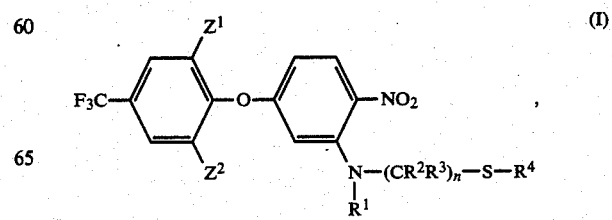

where $Z^1$ is hydrogen or halogen, $Z^2$ is halogen, $R^1$, $R^2$ and $R^3$ independently of one another are each hydrogen or $C_1$–$C_4$-alkyl, $R^4$ is $C_1$–$C_{10}$-alkyl or an araliphatic radical of 7 to 10 carbon atoms, and n is a number from 1 to 8.

2. A diphenyl ether of the formula I as defined in claim 1 where $Z^1$ is hydrogen, $Z^2$ is chlorine, $R^1$ is hydrogen, $R^2$ and $R^3$ independently of each other are hydrogen or $C_1$–$C_4$-alkyl, $R^4$ is $C_1$–$C_{10}$-alkyl, and n is a number from 1 to 4.

3. A diphenyl ether of the formula I as defined in claim 1 where $Z^1$ is hydrogen, $Z^2$ is chlorine, $R^1$ is hydrogen, $R^2$ and $R^3$ independently of each other are hydrogen or $C_1$–$C_4$-alkyl, $R^4$ is $C_1$–$C_{10}$-alkyl, and n is a number from 1 to 3.

4. A diphenyl ether of the formula I as defined in claim 1 where $Z^1$ is hydrogen, $Z^2$ is chlorine, $R^2$ is hydrogen, $R^3$ is hydrogen or ethyl, and $R^4$ is methyl.

5. A herbicide containing inert additives and a diphenyl ether of the formula I as defined in claim 1.

6. A herbicide containing inert additives and from 0.1 to 95 wt% of a diphenyl ether of the formula I as claimed in claim 1.

7. A herbicide containing inert additives and a diphenyl ether of the formula I as defined in claim 2.

8. A herbicide containing inert additives and a diphenyl ether of the formula I as defined in claim 3.

9. A herbicide containing inert additives and a diphenyl ether of the formula I as defined in claim 4.

10. A process for combatting the growth of unwanted plants, wherein the unwanted plants or the area to be kept free from unwanted plant growth are treated with a herbicidally effective amount of a diphenyl ether of the formula I as defined in claim 1.

11. 3-[(1,1-dimethyl-2-methylthio)ethylamino]-4-nitro-2'-chloro-4'trifluoromethyl-diphenyl ether.

* * * * *